United States Patent [19]
Cameron

[11] Patent Number: 5,197,954
[45] Date of Patent: Mar. 30, 1993

[54] HYPODERMIC SYRINGE HAVING FOLDING NEEDLE

[76] Inventor: Robert W. Cameron, 1321 King St., Bellingham, Wash. 98226

[21] Appl. No.: 774,566

[22] Filed: Oct. 9, 1991

[51] Int. Cl.⁵ .......................... A61M 5/00; A61M 5/32
[52] U.S. Cl. .................................. 604/110; 604/187; 604/192; 128/919
[58] Field of Search ................. 604/93, 110, 111, 240, 604/242, 218, 222, 243, 192–199, 187, 263; 128/919, 642, 785

[56] References Cited

U.S. PATENT DOCUMENTS

| | | | |
|---|---|---|---|
| 3,320,954 | 5/1967 | Cowley | 604/110 |
| 4,858,623 | 8/1989 | Bradshaw et al. | 128/785 |
| 4,907,600 | 3/1990 | Spencer | 604/240 |
| 4,917,243 | 4/1990 | Abrams et al. | 604/192 |

Primary Examiner—Randall L. Green
Assistant Examiner—Paul Zuttarelli
Attorney, Agent, or Firm—Hughes & Multer

[57] ABSTRACT

A hypodermic syringe having a needle which folds back into a longitudinally extending channel formed on the side of the barrel of the syringe after use. A disinfectant pad may be mounted in the channel for sterilizing the needle, and lugs are provided for retaining the needle in the channel. During use, the needle is mounted to the lower end of the syringe by a supporting boss. This boss may be provided with a relatively weaker portion so that it snaps off from the barrel of the syringe in response to lateral pressure. Alternatively, there is a releasable catch which holds the boss in abutment with the end of the barrel. After the boss is separated from the end of the barrel, a pivot hinge which is mounted to the boss permits it to be folded into the protective channel.

22 Claims, 4 Drawing Sheets

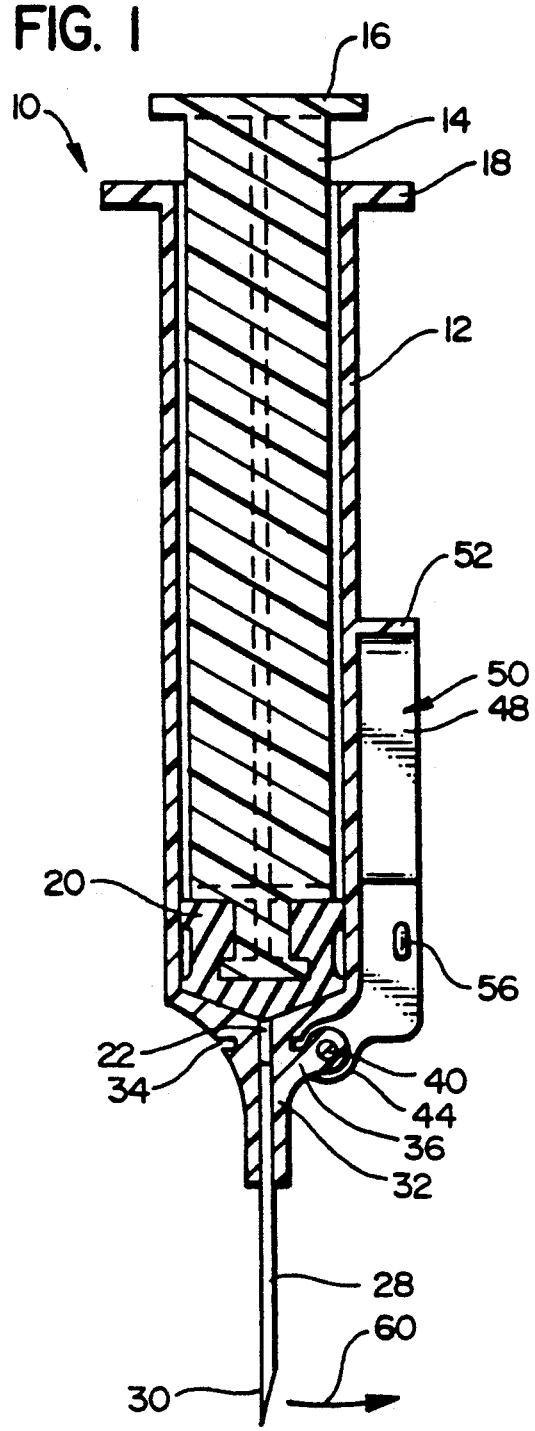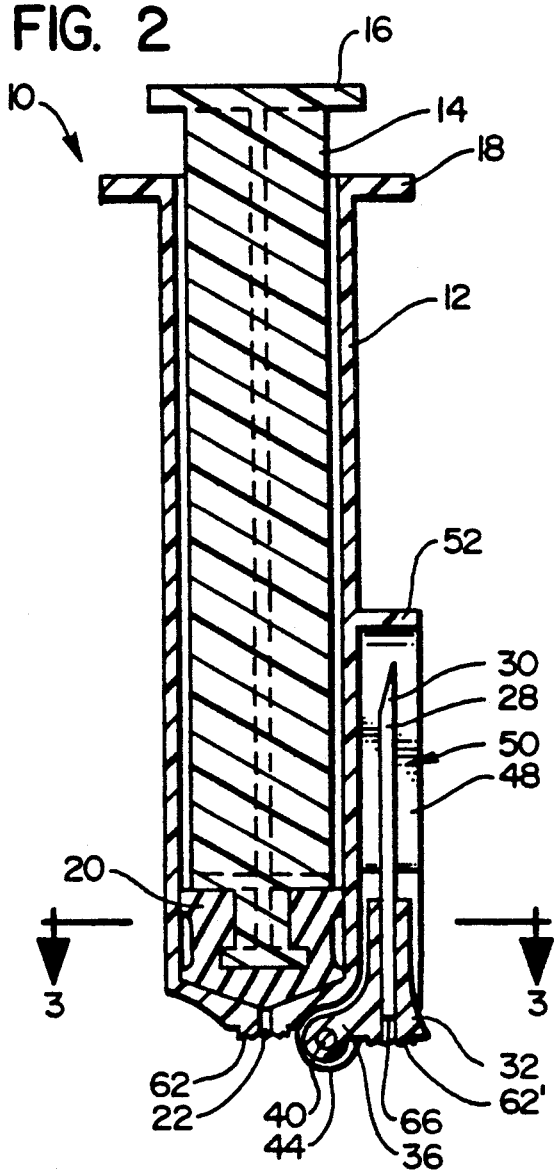

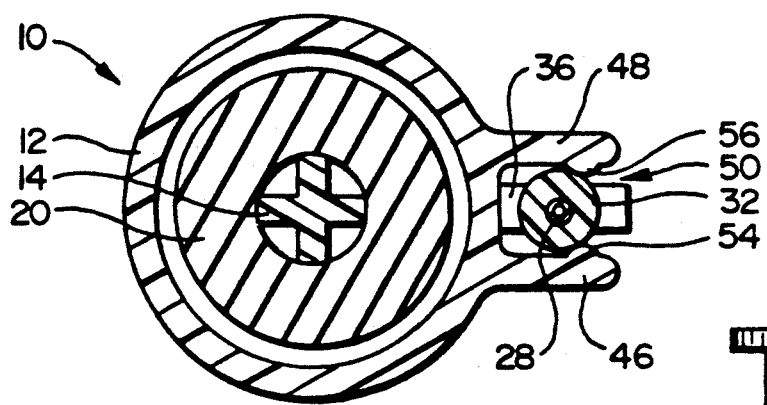
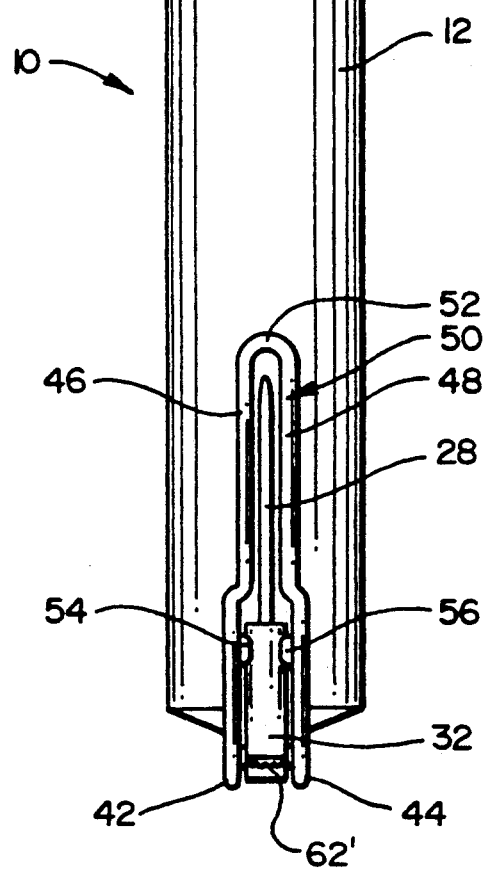

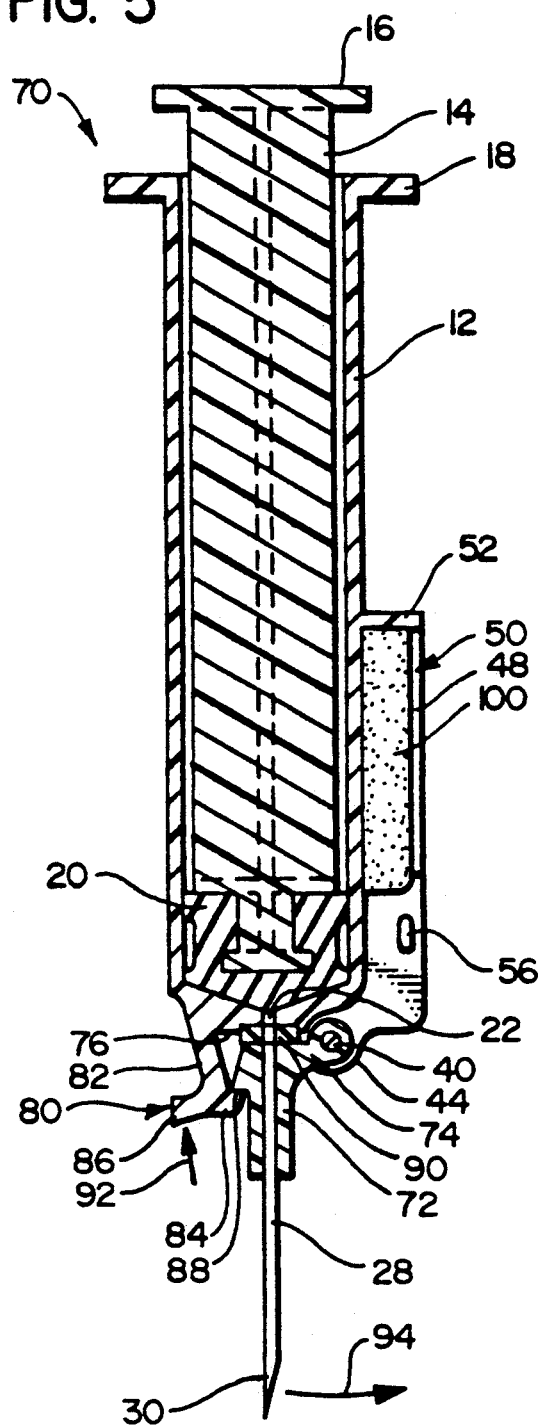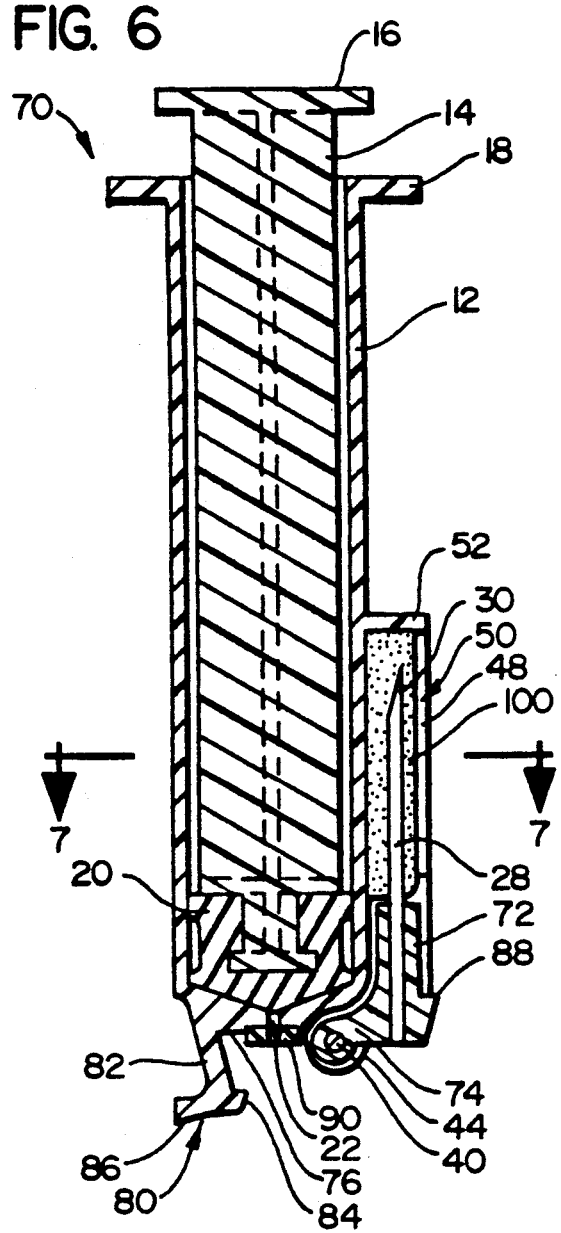

HYPODERMIC SYRINGE HAVING FOLDING NEEDLE

FIELD OF THE INVENTION

The present invention relates generally to hypodermic syringes, and, more particularly, to a hypodermic syringe having a needle which snaps off and folds back into a protective groove in the side of the syringe so as to prevent both accidental injury and re-use.

BACKGROUND OF THE INVENTION

Discarded hypodermic syringes present a serious health hazard. It is not unusual for people to be accidentally pricked by the needle of the syringe after use, and so become infected with a disease which has been transmitted from the person to whom the shot was originally administered. For example, personnel cleaning up hospital spaces or doctors' offices frequently must pick up numerous such syringes after use, and it is very easy to be accidentally pricked or stuck by the needle when doing this. Furthermore, used hypodermic syringes are frequently disposed of in plastic garbage bags, and these are readily pierced by the needles so that these are exposed and can easily prick a person who is handling the garbage bags. Also, municipal garbage is frequently dumped at sea, and there have been cases where syringes have washed up on the beach, where they may be stepped on by barefoot strollers. The seriousness of this problem has been heightened by the spread of the Acquired immune Deficiency Syndrome (AIDS) virus. Not only are diseases such as this spread by the accidental pricking of persons after the syringe has been used, but some persons, notably habitual drug abusers, frequently re-use syringes, without taking the necessary steps to ensure their sterility.

Some attempts have been made to eliminate the problems of re-use and accidental injury from used hypodermic syringes. Some syringes have needles which unscrew from the barrel of the syringe after use, but this is inconvenient, and the loose needles continue to present a hazard. Also, devices have been provided which cut or snap the metal needle off from the plastic body of the syringe, both to prevent its re-use, and also to retain the severed needle in a suitable, relatively thick-walled disposal container. While this provides a relatively satisfactory solution for some facilities, it is not without its drawbacks. For example, hospitals and many doctors' offices have a great many treatment rooms, and it is simply not practical to install a needle clipping device in each of these rooms, for the relatively occasional use which it will receive. More seriously, paramedics and other emergency response personnel who must administer injections at an accident or other emergency scene obviously cannot be burdened with carrying an additional piece of equipment in the form of a needle clipper, and, in any event, they typically do not have time to use such device; this problem is seriously aggravated at many emergency sites, such as automobile accidents, where the paramedic often must work in a confined space or lie on the ground in close proximity with the used hypodermic syringes, and so be at increased risk of being pricked by one of these. A similar situation is faced by military medical personnel in combat situations, and also in military field hospitals.

Accordingly, there exists a need for a hypodermic syringe which provides for protection against injury due to accidental pricking by the point of the used needle, which also prevents reuse of the syringe, without requiring a separate of equipment for doing this. Furthermore, there is a need for a hypodermic syringe having such provisions which is both inexpensive to manufacture and simple to operate.

SUMMARY OF THE INVENTION

The present invention has solved the problems cited above, and comprises generally a hypodermic syringe having a needle which folds against the side of the syringe after use. There is a tubular barrel having an upper end and a lower end, with a plunger member being mounted in this. The hypodermic needle is connected to the lower end of the tubular barrel by connecting means so that the needle extends outwardly therefrom and is in fluid communication with the barrel during initial use of the syringe, with the connecting means being configured for selectively disconnecting the needle from the lower end of the barrel after the initial use. Hinge means are provided for retaining the disconnected needle to the barrel so as to permit the needle to be folded back against the side of the barrel. Receiving means are mounted to the side of the barrel for receiving the needle as this is folded back against the side of the barrel, and for retaining the needle therein. The receiving means may be configured to cover a tip portion of the needle which is retained therein so as to prevent accidental injury due to persons being pricked by this needle after use, and this receiving means may comprise a longitudinally extending channel formed on the side of the barrel of the syringe.

In some embodiments, the means for connecting the needle to the end of the barrel of the syringe may comprise a boss for connecting an end of the needle to the lower end of the barrel, this boss having a relatively weaker portion which is configured to break from the lower end of the barrel in response to selective application of lateral force to the hypodermic needle after its initial use. The boss may be formed integrally with the lower end of the barrel, and the relatively weaker portion may be formed by a groove in the boss. A longitudinally extending bore may pass through the boss for connecting the hypodermic needle in fluid communication with the barrel of the syringe, and, if the hypodermic needle is a metallic needle, the end of t his may be mounted in the bore at an axially lower position than the relatively weaker portion of the boss, so as to avoid the metallic needle interfering with the boss breaking from the lower end of the barrel at the relatively weaker portion.

In other embodiments, the means for connecting the needle to the barrel may comprise another boss for supporting an end of the needle, this having an internal bore in fluid communication with the needle, and releasable means for retaining the boss in abutment with the lower end of the barrel so as to establish fluid communication between the barrel and the bore in the boss. There may also be means for sealing the boss in abutment with the lower end of the barrel, and this sealing means may be a resilient O-ring. The means for retaining the boss in abutment with the end of the barrel may comprise a shoulder portion which extends laterally from the boss, and a releasable latch means for engaging the shoulder portion of the boss. This releasable latch means may comprise an extension arm which extends generally longitudinally from the lower end of the barrel and a catch member which extends generally laterally from the extension arm so as to abut the shoulder portion of the boss. Means are provided for selectively disengaging the catch member from abutment with the shoulder portion of the boss, and this disengaging means may be a tab portion which extends laterally from the extension arm generally opposite the catch member, this tab portion being configured so that in response to generally upwardly directed pressure thereon, the extension arm flexes away from the boss so that the catch member disengages from abutment with the shoulder portion of the boss.

The hinge means which permits the needle to be folded back against the barrel may comprise an arm member mounted to a base portion of the needle, this having a laterally extending outer end which is connected by a pivot pin to the barrel for pivoting movement.

There may also be disinfectant means mounted in the longitudinally extending channel in the side of the barrel for sterilizing the hypodermic needle when this is folded into the channel after use. This disinfectant means may comprise a pad of material which is mounted in the channel so as to come into contact with the needle, this pad being impregnated with a disinfectant material which is adapted to sterilize the needle. The pad may be formed of a resiliently compressible material which is configured so that the needle becomes embedded in the disinfectant pad when it is folded into the channel.

The syringe may also be provided with locking means for permitting the needle to be pressed into the longitudinally extending channel on the side of the barrel and then retaining the needle therein, and these locking means may comprise at least one inwardly extending lug which is mounted proximate the lateral opening into the channel, this lug being configured to flex outwardly as the needle is pressed into the channel, and to then flex inwardly after the needle has been pressed into the channel so as to retain the needle therein.

Objects and advantages of the invention not clear from the above will be understood by a reading of the detailed description of the invention and a review of the accompanying drawings.

BRIEF DESCRIPTION OF THE DRAWINGS

FIG. 1 is a view of a longitudinal cross-section through a hypodermic syringe in accordance with the present invention, this having a needle supported by a break-away boss which is hinged so as to fold to one side after separation from the main barrel of the syringe;

FIG. 2 is a cross-sectional view similar to FIG. 1, showing the separated needle of the syringe having been folded back into a protective channel-like receptacle in the side of the syringe;

FIG. 3 is view of a transverse cross-section taken along line 3—3 of FIG. 2, showing the inwardly projecting lugs which retain the needle in the protective receptacle after use;

FIG. 4 is an elevational view of the syringe of FIGS. 1-2, this view being rotated 90° relative to the axis of the syringe from the views of FIGS. 1-2, showing the needle of the syringe retained in its protective receptacle;

FIG. 5 is a cross-sectional view similar to FIG. 1, showing a syringe in accordance with a second embodiment of the present invention, this having a pivoting needle portion which is sealed at its base to the body of the syringe by an O-ring, and which is held in this position by a releasable catch;

FIG. 6 is a cross-sectional view similar to FIG. 5, this showing the catch having been released and the needle having been folded back into its protective receptacle, in this embodiment the protective receptacle being fitted with a resilient pad which is impregnated with a disinfectant material for sterilizing the needle after use;

DETAILED DESCRIPTION

Figure 7:
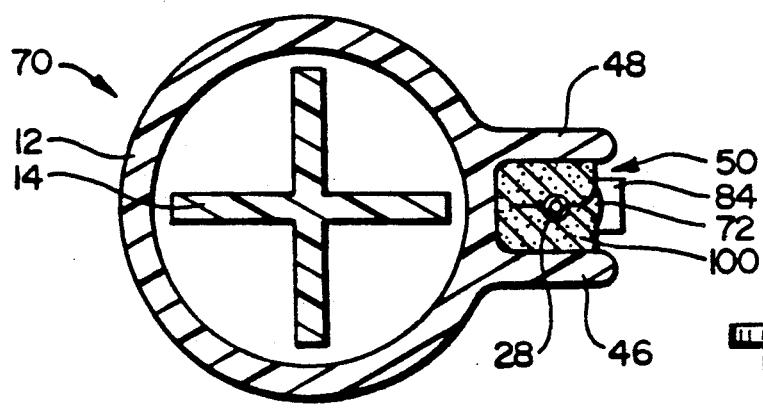
FIG. 7 is a view of a transverse cross-section taken along line 7—7 of FIG. 6, showing the needle embedded in the resilient disinfectant pad in the protective receptacle.

FIG. 1 shows a syringe 10 incorporating the present invention. This has a generally conventional tubular barrel portion 12 in which a plunger member 14 is received for longitudinal movement. A circular head 16 on the upper end of plunger 14 and a circumferential flange 18 on the upper end of barrel portion 12 are configured to be manipulated by the fingers of an operator, so that a seal member mounted at the lower end of plunger 14 moves through the barrel so as to force fluid out of the barrel through a bore 22 at its lower end in a conventional manner.

At this point it should be noted that the term "lower", as used in this description and the appended claims, refers to that end of the syringe which is directed towards the skin of the patient for injection of the fluid (i.e., the needle end), while the term "upper" refers to the opposite.

The fluid which is ejected through bore 22 enters hypodermic needle 28 which, in a conventional fashion, has a sharp tip portion 30 which is configured to enter under the skin of a patient. Needle 28 is supported about its base by a boss 32, which, in the embodiment illustrated, is formed unitarily with the material of barrel portion 12. For example, these may be formed of relatively rigid plastic or other suitable material (e.g., glass). Where the base of boss 32 meets the lower end of barrel 12, there is a circumferential score or groove 34 which provides a relatively weak point which ensures that boss 32 will break off and separate from barrel 12 at this point in response to the former being submitted to sufficient lateral pressure; the base of the metallic needle 28 stops short of groove 34 (i.e., the upper end of the metallic needle 28 is positioned in bore 22 below the level of groove 34), so as to avoid this interfering with the boss snapping off at this point.

An arm portion 36 extends laterally from boss 32, and the end of this is mounted by a pivot pin 40 to first and second upstanding wall portions 42, 44 (44 only shown in FIG. 1, but both wall portions being shown in FIG. 4) so as to permit boss 32 to pivot laterally and upwardly about pivot pin 40 once separated from the base of barrel 12.

The upstanding wall portions 42, 44 continue upwardly from the lower end of barrel 12, and extend generally parallel to one another along the side of the sleeve so that the upper portions 46, 48 thereof (upper portion 48 only being shown in FIG. 1) form a longitudinally extending, channel-like receptacle 50 which is configured to receive boss 32 at its lower end and needle 28 towards its upper end, the upper end of receptacle 50 being closed by an end wall 52 which joins the two parallel side wall portions 46, 48. First and second inwardly projecting lugs 54, 56 (56 only being shown in FIG. 1) are also mounted to the side walls of the receptacle, these being configured to retain needle 28 in receptacle 50, and to yield outwardly so as to permit the needle to be pressed into the receptacle, as will be described in greater detail below.

Having described the major components of syringe 10, the manner of its operation will now be described. The filling of the syringe and its use to inject the fluid into the patient is carried out in the same manner as for conventional syringes. Then, after its initial use, the operator exerts lateral force against needle 28 and its supporting boss 32 in the direction indicated by arrow 60. Preferably, this is done by striking or pressing needle 28 against an available surface, such as a desktop or the ground, or possibly by pressing against the side of a needle with a finger. As this is done, the base of boss 32 separates from the base of sleeve 12 at groove 34; as may be seen in FIG. 2, this area forms what may be considered to be a weakened "O-ring" 62, which breaks or snaps in two transversely as the boss pivots downwardly and laterally in response to the pressure which is exerted against the side of the needle (the two halves of the broken O-ring being indicated by numerals 62, 62' in FIG. 2). As noted above this "O-ring" may be unitarily formed with the barrel and the supporting boss, as of relatively rigid, brittle plastic; alternatively the "O-ring" 62 may be a separate component which is constructed to snap off in the manner described. As is also clearly shown in FIG. 2, the end 66 of the metallic needle 28 is positioned a short axially-spaced distance from the level of the breakable O-ring 62 so as to avoid interfering with this snapping in two as.

Once the base of boss 32 has been separated from sleeve 12, the operator rotates boss 32 and needle 28 about pivot pin 40 in a lateral and upward direction towards the protective receptacle 50. When the boss and needle reach the opening of receptacle 50, a slight resistance is offered by the inwardly extending locking lugs 54, 56 to overcome this, the operator simply increases the pressure against the outer side of the needle and boss, in response to which the lugs yield outwardly so as to permit the boss and needle to enter the receptacle. Once the boss and needle have been fully received within the receptacle, the locking lugs 54, 56 rebound back inwardly toward one another so as to narrow the opening and prevent the needle from accidentally rotating back out of the receptacle. Thus positioned in receptacle 50, the needle is protected against accidental injury to persons handling the used syringe by the surrounding walls 46, 48, 52, with end wall 52 in particular being sufficiently close to the sharp tip portion 30 of the needle to prevent a person's finger or other body part from moving axially into contact with this so as to be pricked by the sharp point. Also, because the separation of the base of the boss 32 from sleeve 12 has irreparably broken the "O-ring" 62, the syringe 10 is rendered totally inoperable, preventing its subsequent reuse.

FIG. 3 is a view of a transverse cross-section taken through syringe 10, showing how needle 28 and its associated support boss 32 are retained in protective receptacle 50. In particular, FIG. 3 shows how parallel wall portions 46 and 48 are spaced apart from one another laterally so as to form a channel having a width sufficient, towards its lower end, to accommodate the width of the boss 32. However, the first and second lugs 54, 56 project inwardly from these walls by a distance sufficient to reduce the gap at this point to a width slightly less than that of the boss. The inner ends of the two lugs are rounded (or otherwise configured) so that they react against the cylindrical outer wall of boss 32 as this is pressed into receptacle 50 so as to yieldingly flex wall portions 46, 48 outwardly, increasing the gap at this point and admitting boss 32 and needle 28 into receptacle 50. As the boss 32 is pressed further into receptacle 50, the lugs 54, 56 pass its widest point, and the side wall portions 46, 48 flex back inwardly, narrowing the gap again so as to prevent needle 28 and boss 32 from rotating back out of the receptacle. Furthermore, because the end of boss 32 is mounted to the side walls by pivot pin 40, the needle cannot be withdrawn longitudinally out of the receptacle either.

Although in the embodiment illustrated in FIGS. 1-3 the receptacle 50 is formed by upstanding wall portions which extend outwardly from the barrel of the syringe, it will be understood that the receptacle may also be formed as a recessed groove in the wall of the barrel itself, with the depth of the groove being accommodated by the thickness of the wall material, or possibly by forming an accommodating recess in the plunger member within the barrel.

FIG. 4 shows an exterior view of syringe 10, looking directly at the protective receptacle 50 as this retains needle 28. In particular, FIG. 4 shows that, While the upper wall portions 46, 48 extend generally parallel to one another so as to form the channel-like receptacle, they are spaced relatively wider from one another in the lower part of the receptacle so as to provide sufficient width in this area to accommodate the relatively wide boss 32, while towards the upper end of the receptacle the wall portions are spaced closer to one another so that the receptacle is narrower in this area and fits closely about the relatively narrow needle 28. By thus fitting very closely about both the boss 32 and the needle 28 when these are positioned in receptacle 50, the walls make it very difficult to extract the needle from the receptacle once it has been snapped into this. For example, it would be very difficult to insert a fingernail between the needle and the wall adjacent to it so as to be able to pull the needle and its boss back out through the retaining lugs 54 and 56. This significantly reduces the possibility that children or other persons will be able to extract the used needle from its protective receptacle and accidentally harm themselves.

FIG. 4 also shows the manner in which boss 32 is mounted to the lower portions of parallel walls 42, 44 by pivot pin 40.

FIGS. 5-8 illustrate a second syringe incorporating the present invention, in which embodiment the pivoting needle boss is retained in position during its initial use by a releasable catch. Inasmuch as numerous members (e.g., sleeve 12, plunger member 14, etc.) are shared by this embodiment and that which has been previously described, like reference numerals will refer to like elements in both FIGS. 1-4 and FIGS. 5-8.

Accordingly, FIG. 5 shows a syringe 70 having a sleeve portion 12 and a plunger member 14. As with the previously described syringe, the fluid is ejected through a bore 22 at the lower end of the barrel, and this bore is contiguous with the a hypodermic needle 28 through which the fluid is injected into the patient. The base of the needle is supported by a boss 72. As with the boss 32 described above, boss 72 has an arm portion 74 which is pivotally mounted to upstanding walls 42, 44 by pivot pin 40. However, in this embodiment, the base of boss 72 is retained in sealing abutment with the base 76 of barrel 12 by a releasable catch 80. Catch 80 comprises an extension arm 82 which extends downwardly from the base 76 of the barrel and a hook portion 84 which extends laterally from this towards the needle support boss 72. A release tab 86 is also mounted on the end of extension arm 82, and extends outwardly from boss 72 generally opposite hook portion 84. Catch 80, and particularly extension arm 82, is preferably fabricated of a suitable semi-rigid material possessing a limited degree of flexibility, or of a brittle material which snaps off when subjected to sufficient bending stress.

As noted above, hook portion 84 of catch 80 extends towards boss 72; this abuts and engages a locking shoulder 88 which extends laterally from boss 72, so as to hold the base of boss 72 firmly against the base 76 of the barrel portion of the syringe. An O-ring member 90 is sandwiched between the base of boss 72 and the base 76 of the barrel. O-ring member 90 may be, for example, a frangible O-ring which is fused to the barrel portion and the needle boss; in this case, the catch 80 which holds the needle boss firmly against the base of the sleeve member helps enable this embodiment of the invention to utilize an O-ring member which separates or breaks much more easily at the desired time (i.e., when the catch is released after use) than is the case in the embodiment described above, where the O-ring member alone must support the boss and needle throughout the use of the syringe. As an alternative, O-ring member 90 may be a separate, resilient member, for example, resilient rubber O-ring or other gasket or sealant material, with this being held in compression between the boss and the base of the sleeve portion by the catch 80, so that after catch 80 is released, the needle 28 and base member 72 would swing away with little resistance.

After using syringe 70, to fold the needle away and stow it in its protective receptacle 50, the operator simply presses upwardly on the release tab 86 of catch 80, in the direction indicated by arrow 92; this flexes extension arm 82 so that hook portion 84 moves away from abutment with the locking shoulder 88 on boss 72. Alternatively, the arm may be constructed to break off when bent in this manner. Also, in some embodiments, it may be desirable to configure catch 80 so that this may be released without requiring the separate step of manipulating the release tab with the finger, as, for example, by configuring the hook portion 84 to be in yielding engagement with the locking shoulder 88 on the boss, so that the catch can be released by simply applying adequate lateral force to the needle and boss.

Once the hook portion and locking shoulder have moved out of engagement, the operator simply presses the needle and boss 72 in the direction indicated by arrow 94, and the base of boss 72 separates from the base of the barrel of the syringe, breaking the seal formed by O-ring member 90. The operator then continues to rotate the needle and its boss in the direction indicated by arrow 94 in the manner previously described until the needle and boss enter protective receptacle 50, at which point additional pressure forces these past locking lugs 54, 56 and into the receptacle.

In the embodiment illustrated in FIGS. 5-8, protective receptacle 50 is at least partially filled with a soft, resilient disinfectant pad 50. This disinfectant pad may be formed of any suitable resilient material (e.g., foam rubber), and is impregnated with a suitable disinfectant material for destroying pathogens on needle 28 upon contact therewith. One suitably effective and inexpensive material for this purpose may be dried, powdered bleach material, this being activated by contact with residual moisture on needle 28 and having been found effective at destroying the AIDS virus, amongst other pathogens, although many other suitable disinfectant materials are of course known to those skilled in the art. As needle 28 and its supporting boss are forced into the receptacle 50, needle 28 becomes at least partially embedded in the disinfectant pad, with the result that disinfectant pad 100 comes into contact with needle 28 and sterilizes it, destroying the pathogens thereon.

Figure 8:
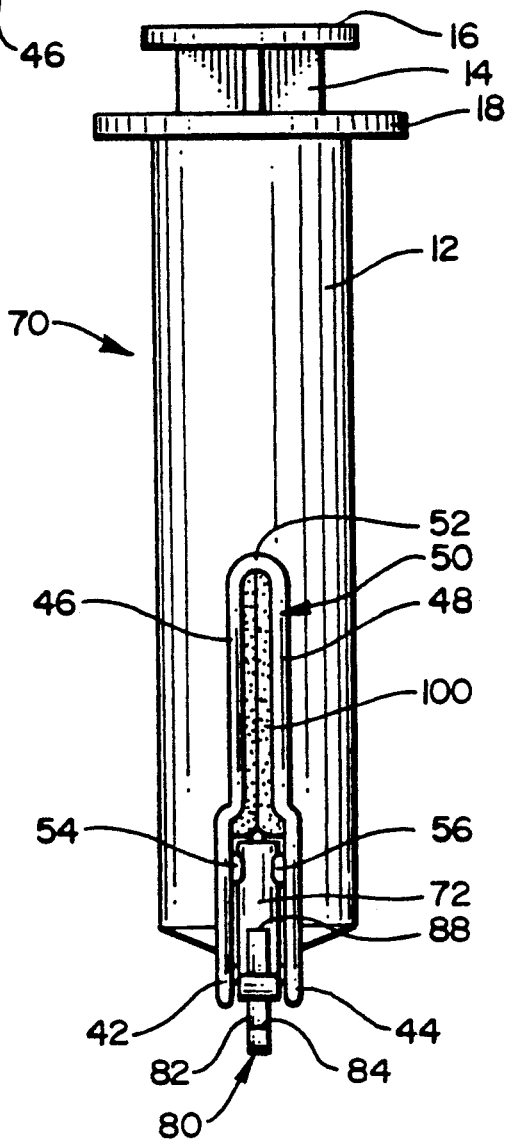
FIG. 8 is an elevational view similar to that of FIG. 4, also showing the needle embedded in the disinfectant pad in the protective receptacle.

This embedment of needle 28 in disinfectant pad 100 is also clearly shown in FIGS. 7-8. In both of these views, it will be seen that, as the needle 28 is pressed into the disinfectant pad 100, it is essentially enclosed by the material of the pad, the resilient material expanding again once the needle has moved past it so as to substantially close the gap on the outer side of the needle. This ensures effective contact of the disinfectant pad with virtually the entire surface of the needle. To facilitate this, it may be desirable to provide the disinfectant pad 100 with a performed groove or slit which is sized to receive the needle as it is pressed into the protective receptacle 50.

Having described the invention in its preferred embodiments, it will be clear that changes and modifications may be made thereto without departing from the spirit of the invention. It is therefore not intended that the words used to describe the invention or the drawings illustrating the same be limiting on the invention. Rather, it is intended that the invention only be limited by the scope of the appended claims.

What is claimed is:

1. A hypodermic syringe comprising:
   a tubular barrel having an upper end and a lower end;
   a plunger member mounted in said tubular barrel for ejecting fluid from said barrel;
   a hypodermic needle for injecting into a person said fluid ejected from said barrel;
   connecting means for connecting said hypodermic needle to said lower end of said tubular barrel so that said needle extends outwardly from said lower end of said barrel and is in fluid communication therewith during an initial use of said syringe, and for selectively disconnecting said needle from said lower end of said barrel after said initial use;
   hinge means for retaining said disconnected needle to said barrel so as to permit said needle to be folded back against a side of said barrel; and
   receiving means mounted to said side of said barrel for receiving said needle which is folded back against said side of said barrel and for retaining said needle therein.

2. The hypodermic syringe of claim I, wherein said receiving means is configured to cover a tip portion of said hypodermic needle which is retained therein so as to prevent accidental injury due to persons being pricked by said tip portion of said needle after use.

3. The hypodermic syringe of claim 2, wherein said receiving means comprises a longitudinally extending channel formed on said side of said barrel.

4. The hypodermic syringe of claim 3, wherein said connecting means comprises,
   a boss for connecting an end of said needle to said lower end of said barrel, said boss having a relatively weaker portion which is configured to break from said lower end of said barrel in response to selective application of lateral force to said hypodermic needle after said initial use.

5. The hypodermic syringe of claim 4, wherein said boss is integral with said lower end of said barrel.

6. The hypodermic syringe of claim 5, wherein said relatively weaker portion is formed by a groove formed in said boss.

7. The hypodermic syringe of claim 6, wherein said groove is formed circumferentially about said boss.

8. The hypodermic syringe of claim 5, wherein said boss is provided with a longitudinally extending bore for connecting said hypodermic needle in fluid communication with said barrel.

9. The hypodermic syringe of claim 8, wherein said hypodermic needle is a metallic needle, said end of said needle being mounted in said bore in said boss at an axially lower position than said relatively weaker portion, so as to avoid said metallic needle interfering with said boss breaking from said lower end of said barrel at said relatively weaker portion.

10. The hypodermic needle of claim 3, wherein said connecting means comprises:
- a boss for supporting an end of said hypodermic needle, said boss having an internal bore in fluid communication with said hypodermic needle; and
- releasable means for retaining said boss in abutment with said lower end of said barrel so as to establish fluid communication between said barrel and said bore in said boss.

11. The hypodermic syringe of claim 10, further comprising means for forming a seal between said barrel and said boss in abutment with said lower end of said barrel so as to prevent said ejected fluid from escaping between said boss and said lower end of said barrel.

12. The hypodermic needle of claim 10, wherein said releasable means for retaining said boss in abutment with said lower end of said barrel comprises:
- a shoulder portion extending laterally from said boss; and
- releasable latch means for engaging said shoulder portion of said boss so as to hold said boss in abutment with said lower end of said barrel.

13. The hypodermic needle of claim 12, wherein said releasable latch means comprises,
- an extension arm extending generally longitudinally from said lower end of said barrel; and
- a catch member extending generally laterally from said extension arm so as to abut said shoulder portion of said boss.

14. The hypodermic syringe of claim 13, wherein said releasable latch means further comprises means for disengaging said catch member from abutment with said shoulder portion of said boss.

15. The hypodermic syringe of claim 14, wherein said means for disengaging said catch member from abutment from said shoulder portion of said boss comprises a tab portion which extends laterally from said extension arm generally opposite said catch member, said tab portion being configured so that in response to generally upwardly directed pressure on said tab member, said extension arm flexes away from said boss so that said catch member disengages from abutment with said shoulder portion of said boss.

16. The hypodermic syringe of claim 11, wherein said means for forming a seal between said boss and said lower end of said barrel comprises a resilient O-ring.

17. The hypodermic syringe of claim 3, wherein said hinge means comprises:
- an arm member having an inner end mounted to a base portion of said hypodermic needle, and a laterally extending outer end; and
- a pivot pin connecting said outer end of said arm member to said barrel for pivoting movement of said hypodermic needle from an outwardly extended position to a position in which said needle is folded back against said side of said barrel.

18. The hypodermic syringe of claim 3, further comprising disinfectant means mounted in said longitudinally extending channel on said side of said barrel for sterilizing said hypodermic needle when said needle is folded into said channel after said initial use.

19. The hypodermic syringe of claim 18, wherein said disinfectant means comprises a pad of material mounted in said channel so as to come into contact with said hypodermic needle when said needle is folded into said channel, said pad being impregnated with a disinfectant material which is adapted to sterilize said needle after said use.

20. The hypodermic syringe of claim 19, wherein said pad of material is a pad of resiliently compressible material configured so that said needle becomes substantially embedded in said disinfectant pad when said needle is folded into said channel.

21. The hypodermic syringe of claim 3, further comprising locking means for permitting said hypodermic needle to be pressed into said longitudinally extending channel and then retaining said needle in said channel.

22. The hypodermic syringe of claim 21, wherein said locking means comprises at least one inwardly extending lug mounted proximate a lateral opening into said channel, said lug being configured to flex outwardly as said needle is pressed into said lateral opening, and to then flex inwardly after said needle has been pressed through said opening so as to retain said needle in said channel.

* * * * *